United States Patent [19]
Griffiths et al.

[11] 4,007,731
[45] Feb. 15, 1977

[54] MEANS AND TECHNIQUES FOR ESTABLISHING HEARING DEFICIENCIES

[76] Inventors: Ciwa Griffiths, c/o Hear Center, 301 E. Del Mar Blvd., Pasadena, Calif. 91101; Dean O. Thompson, c/o Two:Dot Enterprises, 4438 Hendrickson Road, Ojai, Calif. 93023

[22] Filed: Aug. 14, 1975

[21] Appl. No.: 604,898

[52] U.S. Cl. .......................... 128/2 Z; 128/2.06 F; 179/1 N
[51] Int. Cl.² ..................................... A61B 5/12
[58] Field of Search ............. 128/2.1 B, 2 Z, 2 N, 128/2.06 F; 179/1 N

[56] References Cited
UNITED STATES PATENTS

| | | | |
|---|---|---|---|
| 3,392,241 | 7/1968 | Weiss et al. | 128/2 Z X |
| 3,706,308 | 12/1972 | John et al. | 128/2.1 B X |
| 3,718,763 | 2/1973 | Cannon et al. | 179/1 N |
| 3,780,724 | 12/1973 | John | 128/2.1 B |
| 3,799,146 | 3/1974 | John et al. | 128/2.1 B |
| 3,808,354 | 4/1974 | Feezor et al. | 179/1 N |
| 3,837,331 | 9/1974 | Ross | 128/2.1 B |
| 3,901,215 | 8/1975 | John | 128/2.1 B |

Primary Examiner—Kyle L. Howell
Attorney, Agent, or Firm—Lyon & Lyon

[57] ABSTRACT

Neonates are tested for hearing deficiencies. A printed record is made of changes in heart beat rate in response to various sound stimuli. Relevant information such as heart beat rate, frequency of the stimulating sound, intensity of the stimulating sound, and related clock information is printed out in digital form. In a modification, changes in time between heart beats are extrapolated so that, in effect, changes in heart beat rate may be quickly determined on a go-no-go basis. These tests are particularly useful on infants under the age of eight months so that corrective measures may be taken prior to expiration of a critical period of development in the infant's life.

8 Claims, 2 Drawing Figures

MEANS AND TECHNIQUES FOR ESTABLISHING HEARING DEFICIENCIES

The present invention relates to improved means and techniques for determining hearing deficiencies and is particularly useful in testing the hearing of infant's under the age of 8 months.

A specific object of the present invention is to provide a hearing determining system in which changes in heart beat rate in response to sound stimuli may be readily and accurately established and recorded.

Another specific object of the present invention is to provide a system having the features set forth in the preceeding paragraph in which the pertinent data is developed and compared in digital form.

The present invention is based on studies and observations of the hearing ability of children through their infant stage. These studies reveal a critical age of hearing in that should an infant have hearing deficiencies, steps should be taken to intervene and correct such deficiencies before the age of eight months otherwise it may be too late, and the child thereafter, for good hearing, may be required to wear hearing aids.

The present invention has for one of its purposes, the provision of means and techniques whereby such hearing deficiencies may be ascertained in infants under the age of eight months.

The features of the present invention which are believed to be novel are set forth with particularity in the appended claims. This invention itself, both to its organization and manner of operation, together with further objects and advantages thereof, may be best understood by reference to the following description taken in connection with the accompanying drawings in which:

Figure 1:
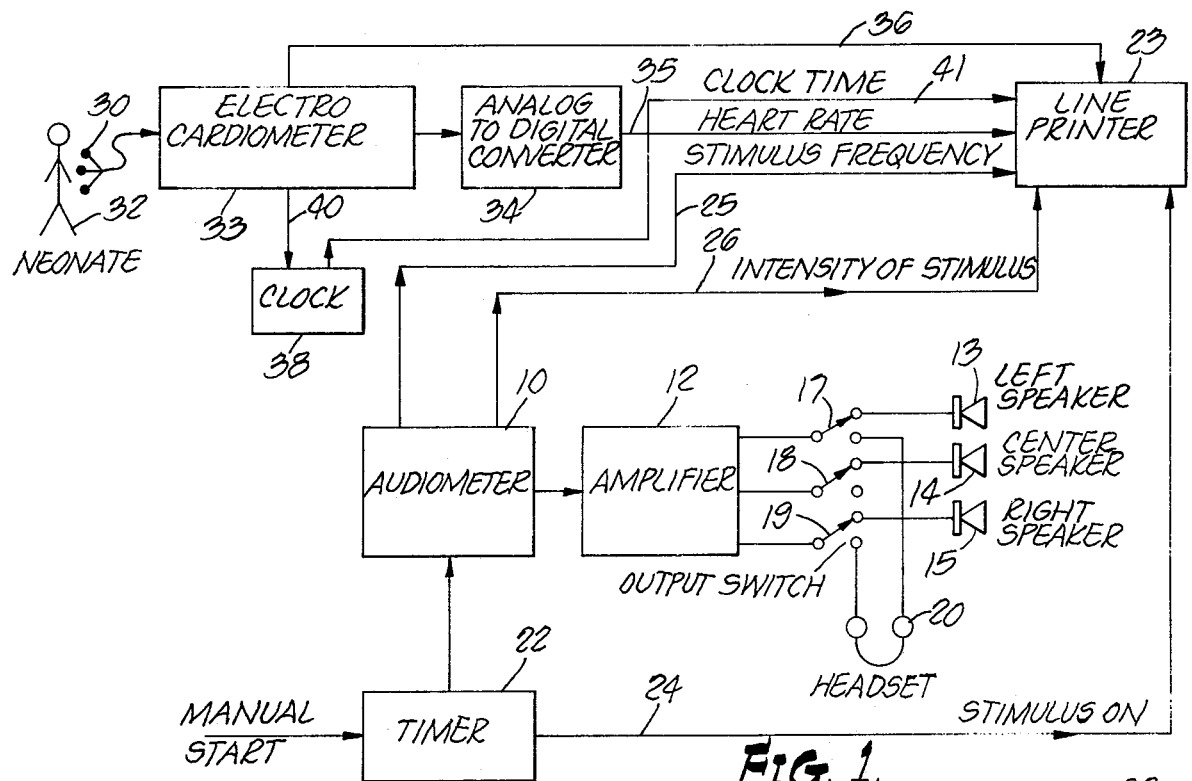
FIG. 1 illustrates a system embodying features of the present invention.

In FIG. 1, the audiometer 10 is a source of sound tones which may, for example, have a frequency of 250, 500, 1000, 2000, 4000, and 6000 hertz. The audiometer 10 is also capable of producing a warble tone for a variance of signals which is in the nature of a frequency modulation with the modulation being plus or minus 10 percent. The audiometer 10 is a conventional sound source and may include a calibrated output attenuator which adjusts the output level of the audiometer so that after amplification in the amplifier 12, the sound output from the transducer which may comprise one or more of the three speakers 13, 14 and 15 is equal to the intensity set in on the attenuator and may, for example, be 30 decibel. Indeed, the attenuator levels may be set from 30 to 110 decibel steps. It is noted that one or more of these speakers 13, 14 and 15 designated respectively as the left, center and right speaker, may be connected to the output of the amplifier 12 through corresponding single poledouble throw switches 17, 18 and 19. Alternately, when the switches 17 and 19 are each in their other position, the sound may be heard in headset 20. The sound so produced by either one of the speakers 13, 14 and 15 is gated on and off by a timer 22. Once the timer 22 is manually started, the timer 22 is effective to cause repetitious bursts of sound with each burst being, for example, of four seconds duration. This on-off condition is recorded on the line printer 23 which receives an output from the timer 22 via lead 24 for that purpose.

The line printer 23 also records or prints characteristics of the sound being produced in the speakers 13, 14 and 15 or headset 20 such as the frequency of the sound as well as the intensity of the sound. For these latter purposes, information as to the frequency and intensity of the sound is supplied to the line printer 23 from the audiometer via corresponding leads 25 and 26.

As designated, the speakers 13, 14 and 15 may be spaced or positioned to the left, center or right of the neonate. The left speaker 13 may be located in the infant bassinette area on the side corresponding to the infant's left ear; the speaker 14 may be located in the bottom beneath the infant's head and is particularly useful when the infant's head is lying to one side; the other speaker 15 may be at the infant's right ear in the bassinette. The headset 20 in the nature of an accessory, may be utilized for infants and children larger than those that can be placed in the bassinette.

As indicated previously, the neonates reaction or lack of reaction to such periodic bursts of sound is also recorded on the line printer 23. For this latter purpose, there is a recording or printing made of the neonate's heart beat rate. The heart beat rate is derived from electrodes 30 which are on the neonate 32 and which are connected to an electrocardiometer 33. This electrocardiometer 33 develops an analog voltage which corresponds to the heart beat rate and such voltage is applied to the analog to digital converter 34 whose output is applied via lead 35 to the line printer 23. The electrocardiometer 33 is the source of printer trigger pulses which appear each time the heart beats and which are applied to the printer 23 via line or lead 36. Also printed on printer 23 is the corresponding time derived from clock 38 which provides a binary coded time output including tenths of seconds, seconds, minutes, and hours whereby information is recorded or printed for time comparison purposes.

Pulses are also supplied from the electrocardiometer 33 via lead 40 for purposes of achieving a reference time, i.e., for initiating the clock time information on lead 41.

Figure 2:
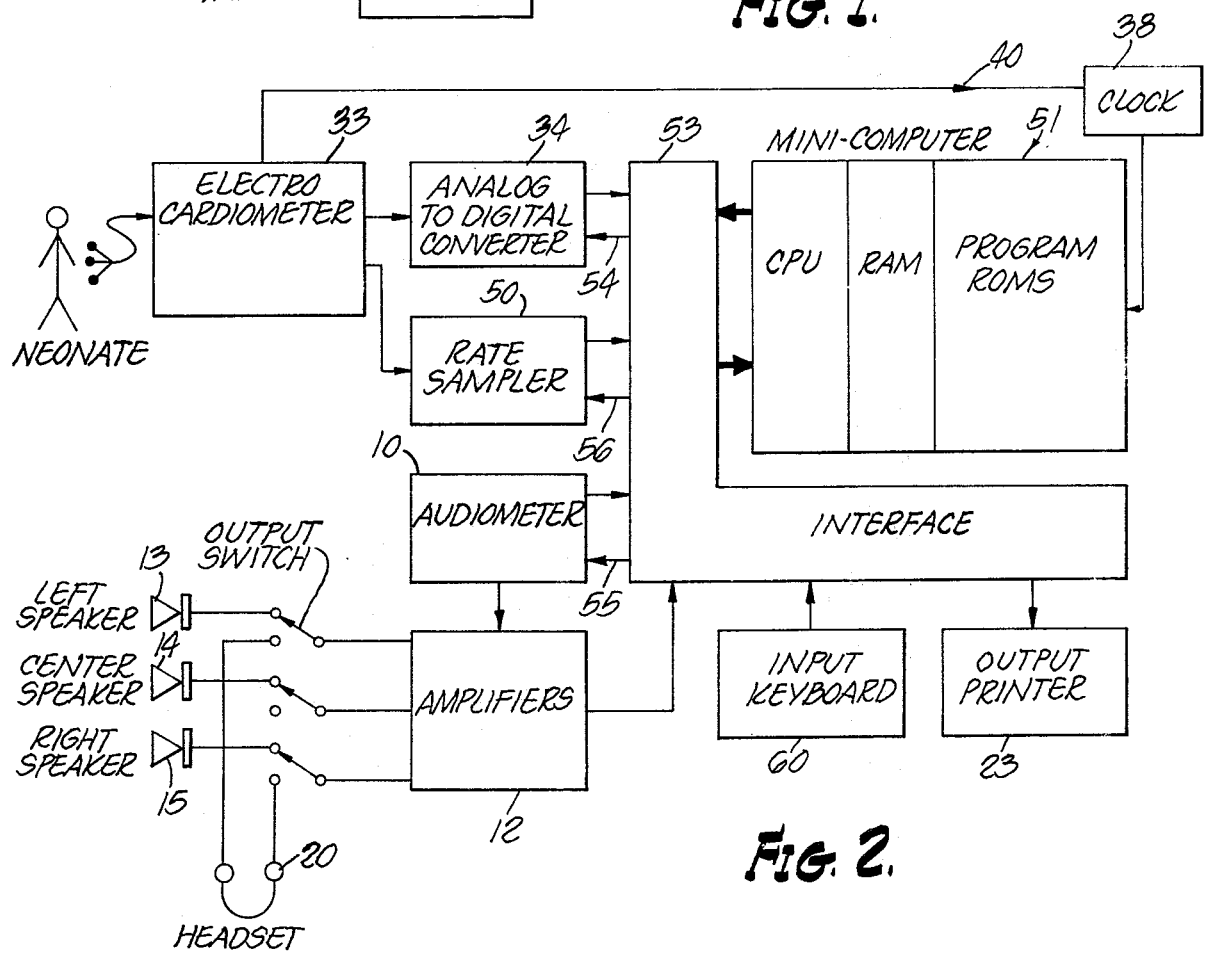
FIG. 2 illustrates a more sophisticated system which includes a computor also embodying features of the present invention.

The arrangement shown in FIG. 2 involves a minicomputor which is particularly useful in deriving information which may be recorded on a go-no-go basis. Corresponding elements in FIG. 1 and 2 have the same reference numerals.

It will be seen in FIG. 2 that the converter 34 and audiometer 10 as well as the rate sampler 50 may be controlled in accordance with information supplied from the mini-computor 51 via the interface unit 53 and corresponding leads 54, 55 and 56.

In FIG. 2 the converter 34 accepts the heart beat rate from cardiometer 33 and converts it to binary digital code which is applied to interface unit 53. The input to converter 34 may be an analog voltage which corresponds directly to the infant's heart beat rate, integrated over a period of time. A second output from the cardiometer 33 is a pulse which appears each time the infant's heart beats and such pulse is amplied to rate sampler 50.

The rate sampler 50, instead of a converter such as converter 34, may be used for these purposes. The rate sampler 50 converts the time period between heart beats into a binary coded heart rate output which is applied to interface unit 53. Because the rate sampler 50 extrapolates the heart rate each time the heart beats, data concerning the heart beat rate is available for instantaneous evaluation without delay.

The interface unit 53 handles communication between the various devices and the computor. It handles both digital data and control signals.

The mini-computor 51 controls and interprets the outputs of the various devices and directs the interface unit 53 to provide a print out interpretation of the tests on output printer 23. The computor 51 includes a central process unit (CPU) which is a binary part of the computor and is used for binary processing of information; also included are random access memories (RAM) used to store data from the tests as the tests progress as well as any intermediate binary outputs of the CPU during interpreting processing; also included are read out memories (Program ROMS) which are programmed and supply the program for the audiometer operation on the computor in regards to test routine and interpretation programs and also to provide special hearing curves for the audiometer 10.

The input keyboard 60 is used to input data and input commands regarding tests to be performed and also the format in which the output should be presented to the output printer.

The output printer 23 in FIG. 2 prints out the data for permanent record of the subject and to communicate to the operator the computor's functions. The output printer 23 is commanded to print by the computer 51 at times when the tests are not being actively conducted, with the problem of noise generated by the printer interfering with the tests being performed being eliminated. The computer 51 may be located remotely from the rest of the equipment and phone communication may be employed using a phone line.

While the particular embodiments of the present invention have been shown and described, it will be obvious to those skilled in the art that changes and modifications may be made without departing from the invention in its broader aspects and therefore, the aim in the appended claims is to cover all changes and modifications as fall within the true spirit and scope of this invention.

We claim:

1. In a system for determining hearing capability, means producing a sound stimulus for a subject whose hearing capability is being established; said means being located in sound range of said subject with such sound stimulus being applied to said subject having the capability of producing changes in activity of the heart of said subject; means attached to said subject when said sound stimulus is being so applied to said subject and producing a first signal representative of the heart beat rate of said subject; means producing a second signal representative of the heart beat of said subject; clock means developing a third signal representative of elapsed time; recording means; means applying said first signal, and said third signal to said recording means for producing a recording representative of said heart beat rate and elapsed time and means applying said second signal to said clock means to initiate said third signal.

2. A system as set forth in claim 1 including means applying signals from said sound producing means to said recording means to effect a recording of the intensity of said sound and also the frequency of said sound.

3. A system as set forth in claim 1 including means for applying said second signal to said recording means to effect the operation of the same.

4. A system as set forth in claim 1 in which said recording means is a line printer and the signals applied thereto for recording are in digital form.

5. A system as set forth in claim 1 including timing means for gating said sound producing means on and off repetitiously, and means applying a signal from said timing means to said recording means to effect a recording representative of the initiation of operation of said sound producing means.

6. In a method for determining hearing capability of a subject, the steps comprising, subjecting said subject to a source of sound; repetitiously turning said sound on and off to produce a train of sound waves for hearing by said subject; and producing a recording of the change in heart beat rate of the subject in response to said train of sound waves.

7. In a method set forth in claim 6, including the step of simultaneously recording the intensity and frequency of said sound waves.

8. In a method as set forth in claim 6, including the steps of simultaneously recording elapsed time between heart beats, and also recording conditions of the sound waves.

* * * * *